(12) United States Patent
Tollini et al.

(10) Patent No.: US 8,128,602 B2
(45) Date of Patent: Mar. 6, 2012

(54) WINGED CATHETER SECURING TAPE (76) Inventors: Dennis R. Tollini, Clarence Center, NY (US); Michael D. Tollini, Clarence Center, NY (US)

( * ) Notice: Subject to any disclaimer, the term of this patent is extended or adjusted under 35 U.S.C. 154(b) by 268 days.

(21) Appl. No.: 12/322,892

(22) Filed: Feb. 9, 2009

(65) Prior Publication Data
US 2009/0143743 A1 Jun. 4, 2009

Related U.S. Application Data (60) Continuation of application No. 10/951,345, filed on Sep. 28, 2004, now abandoned, which is a division of application No. 10/145,506, filed on May 14, 2002, now Pat. No. 6,827,706.

(51) Int. Cl.
*A61M 5/32* (2006.01)
(52) U.S. Cl. ........................................................ 604/180
(58) Field of Classification Search .................. 604/180, 604/174, 177, 179; 128/DIG. 26
See application file for complete search history.

(56) References Cited

U.S. PATENT DOCUMENTS

| 3,288,136 | A | | 11/1966 | Lund |
| 3,834,380 | A | | 9/1974 | Boyd |
| 3,918,446 | A | | 11/1975 | Buttaravoli |
| 4,027,665 | A | | 6/1977 | Scrivens |
| 4,275,721 | A | | 6/1981 | Olson |
| 4,324,236 | A | | 4/1982 | Gordon et al. |
| 4,336,806 | A | * | 6/1982 | Eldridge, Jr. ................ 604/174 |
| 4,460,356 | A | | 7/1984 | Moseley |
| 4,490,141 | A | | 12/1984 | Lacko et al. |
| 4,737,143 | A | | 4/1988 | Russell |
| 4,875,896 | A | | 10/1989 | Kurtz |
| 5,087,248 | A | | 2/1992 | Beisang, III |
| 5,160,315 | A | | 11/1992 | Heinecke et al. |
| 5,304,146 | A | | 4/1994 | Johnson et al. |
| 5,413,562 | A | | 5/1995 | Swauger |
| 5,449,340 | A | | 9/1995 | Tollini |
| 5,685,859 | A | | 11/1997 | Kornerup |
| 6,224,571 | B1 | * | 5/2001 | Bierman ........................ 604/174 |

* cited by examiner

*Primary Examiner* — Manuel Mendez
(74) *Attorney, Agent, or Firm* — Simpson & Simpson, PLLC

(57) ABSTRACT

A winged catheter securing tape including a base having a non-adhesive upper surface and an adhesive lower surface, spaced areas of adhesive on said upper surface with a first non-adhesive area therebetween, and a second non-adhesive area on said lower surface in opposition to said first non-adhesive area.

11 Claims, 11 Drawing Sheets

WINGED CATHETER SECURING TAPE

CROSS-REFERENCE TO RELATED APPLICATIONS

This application is a continuation of U.S. patent application Ser. No. 10/951,345, filed Sep. 28, 2004, now abandoned which is a divisional application of U.S. patent application Ser. No. 10/145,506 filed May 14, 2002, which issued as U.S. Pat. No. 6,827,706 Dec. 7, 2004, which applications are hereby incorporated by reference in their entireties.

FIELD OF THE INVENTION

The present invention relates generally to the field of medical devices, more particularly to the field of securement devices and still more particularly to devices to secure catheters.

BACKGROUND OF THE INVENTION

The present invention relates to a winged catheter securing tape for securing a winged catheter to the skin of a patient without stitching it thereto and without applying it directly to the skin and thereafter taping over it.

By way of background, there are numerous types of winged catheters in medical use. These include subclavian catheters, IJ catheters, femoral catheters, Hickman catheters and fistula needles. The above various types of winged catheters have wings extending outwardly from a central portion thereof. There are two types of wings. One type has holes in the wings, and it is sutured to a patient's skin by passing sutures through holes in the wings and through the skin of the patient. A second type has its wings applied directly to the skin or onto a non-adhesive surface of a tape which is adhesively applied to the skin and is held in position by a tape which passes over the top of the wings. The first type requires direct suturing to the skin. The second type is subject to the deficiency that it may not be held securely in position, and, in certain instances, the wings may irritate the skin when they are applied directly thereto. It is with overcoming the foregoing deficiencies of winged catheters that the present winged catheter securing tape is concerned.

While the winged catheter securing tape of the present invention is applicable to all of the above-mentioned winged catheters, and also to others which have not been mentioned, the following description will be confined to a fistula needle type of winged catheter inasmuch as it is representative of all winged catheters which are defined as "a tubular medical device for insertion into canals, vessels, passageways or body cavities, usually to permit injection or withdrawal of fluids or to keep a passage open. II (Webster's New Collegiate Dictionary, 1973).

BRIEF SUMMARY OF THE INVENTION

The present invention broadly comprises a laminated winged catheter securing tape comprising a tape base having an upper surface and a lower surface, said tape base defining at least one cutout extending from said upper surface through to said lower surface to form an opening therethrough and an adhesive member having an upper side and a lower side wherein said upper side is adhesively attached to at least part of said lower surface of said tape base and an adhesive surface is exposed in at least one of said at least one cutouts.

It is one object of the present invention to provide a winged catheter securing tape which obviates the need for suturing to the skin or relying solely on taping over to hold it in place in direct contact with the skin.

Another object of the present invention is to provide a winged catheter securing tape which is extremely simple in construction.

A further object of the present invention is to provide a winged catheter securing tape which operates in an extremely simple and efficient manner.

A still further object of the present invention is to provide a winged catheter securing tape which can be fabricated in a simple manner.

Yet another object of the present invention is to provide a winged catheter securing tape which can be applied by a patient with one hand. Other objects and attendant advantages of the present invention will readily be perceived hereafter.

The present invention relates to a winged catheter securing tape comprising a base having an upper surface and a lower surface, adhesive on said lower surface facing downwardly, and at least one area of adhesive on said base facing upwardly relative to said upper surface, said at least one area being less than the total expanse of said base.

The various aspects of the present invention will be more fully understood when the following portions of the specification are read in conjunction with the accompanying drawings wherein:

BRIEF DESCRIPTION OF THE SEVERAL VIEWS OF THE DRAWING

The nature and mode of the operation of the present invention will now be more fully described in the following detailed description of the invention taken with the accompanying drawing Figures, in which.

DETAILED DESCRIPTION OF PREFERRED EMBODIMENTS OF THE INVENTION

At the outset, it should be appreciated that like drawing numbers on different drawing views identify identical structural elements of the invention.

While the present invention is described with respect to what is presently considered to be the preferred embodiments, it is understood that the invention is not limited to the disclosed embodiments. The present invention is intended to cover various modifications and equivalent arrangements included within the spirit and scope of the appended claims.

Summarizing briefly in advance, all embodiments of the present invention are for securing a winged catheter to a patient. This is accomplished in several different ways by several different embodiments, all of which eliminate the need for suturing the wings of a winged catheter to a patient's skin or taping over a winged catheter which is in direct contact with the skin, while permitting the winged catheter to be applied to the patient in an extremely simple, expedient and efficient manner and also permitting the winged catheter to be removed in an expedient manner.

The winged catheter securing tape of the present invention will be described hereafter relative to a fistula needle type of winged catheter. The fistula needle is used in a dialysis procedure. In one type of dialysis procedure there is a tube surgically connecting an artery to a vein, and the needle is inserted into the vein which has been enlarged, and which is known as a fistula, to access blood flow. In another type of dialysis procedure a graft is sewn to surgically connect an artery and a vein, and the needle is inserted into the graft. The winged catheter securing tape is intended to be used with a fistula needle type of winged catheter as described above, and the winged catheter securing tape can be used with any type of winged catheter, such as those mentioned above and also others where the winged catheter is to be secured to a patient or to any other type of medical device with which the winged catheter is associated.

Figures 1, 2, 3, 4:
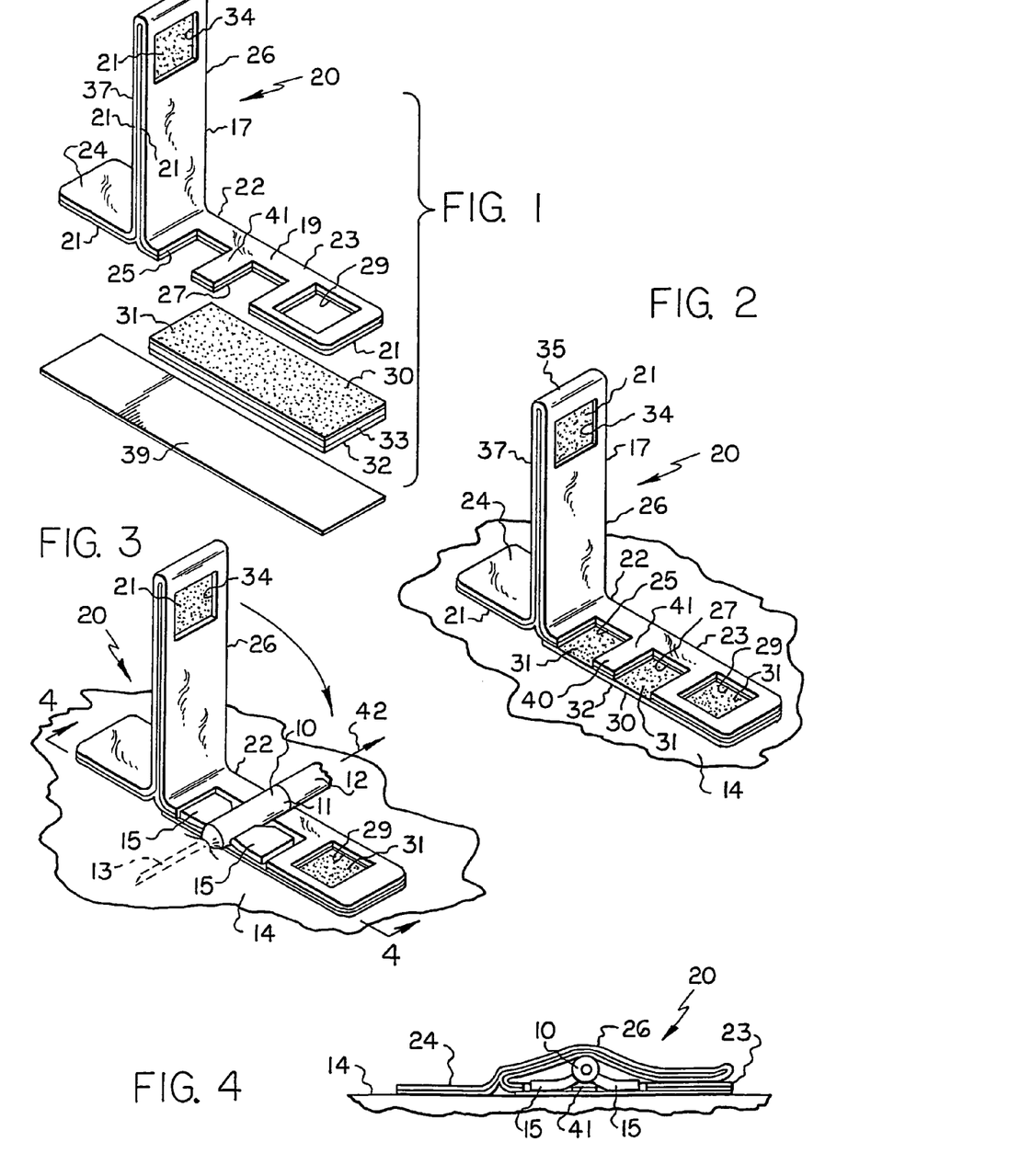
FIG. 1 is an exploded perspective view of one embodiment of the winged catheter securing tape of the present invention.
FIG. 2 is a perspective view of the assembled winged catheter securing tape of FIG. 1 mounted on a patient.
FIG. 3 is a fragmentary perspective view showing the winged catheter securing tape applied to a patient with a winged catheter in the form of a fistula needle in place thereon.
FIG. 4 is an end elevational view taken substantially in the direction of arrows 4-4 of FIG. 3 showing the tab of the winged catheter securing tape in a closed position.

A winged catheter 10 in the form of a fistula needle is shown in FIG. 3, and it includes a central tubular member 11 which is in communication with a tubular catheter 12 leading from an external source. The opposite end of tubular member 11 communicates with a needle 13 which is inserted through the skin 14 into a fistula or graft of a patient. Formed integrally with tubular member 11 is a pair of wings 15 which in the past were either sewn to a patient's skin or taped over without any other securement relative to the patient's skin. The winged catheter which was sewn to the patient's skin had holes in the wings. The type which was taped over merely had wings, as shown, without holes.

One embodiment of the present invention is shown in FIGS. 1-6. The winged catheter securing tape 20 includes a length of adhesive tape 17 having an upper non-adhesive surface 19 and a lower adhesive surface 21. A tab 22 is formed by folding the tape on itself so that the adhesive surfaces 21 adhere to each other. The remainder of the tape is a base 22 consisting of sections 23 and 24. The base 23 has cutouts 25, 27, and 29 therein. A double-sided tape 30 includes an adhesive upper tape surface 31 and an adhesive lower tape surface 32 with a layer of material 33 therebetween. The double-sided tape 30 is adhered in underlying relationship to base portion 23 such that the adhesive surface 31 is exposed through cutouts 25, 27, and 29 to thereby provide adhesive surfaces which face upwardly through the upper surface of base portion 23. The base portion 24 has the adhesive 21 on its lower surface. A cutout 34 is located in one layer of the tab 17 proximate the free end 35 of tab 17 so that the adhesive on the other layer 37 of the tab is exposed. A release paper 39 covers the adhesive surfaces on the lower surface of base 22 and it is removed prior to adhering the base 22 to the patient's skin 14.

In FIG. 3 a winged catheter 10 in the form of a fistula needle is shown in position on the winged catheter securing tape 20 with the wings 15 being adhered to the adhesive surfaces 31 in cutouts 25 and 27. The tubular portion 11 of the winged catheter 10 rests on the non-adhesive surface 40 of peninsula-like base portion 41.

After the base 22 has been applied to the patient 14, as shown in FIG. 3, and the winged catheter 10 has been placed in position thereon, as also shown in FIG. 3, the tab 22 is moved downwardly from the position of FIG. 3 to the position of FIG. 4 whereupon the exposed adhesive 21 in cutout 34 will engage with the exposed adhesive 31 in cutout 29 to additionally securely hold the winged catheter 10 in position. It will be appreciated, however, that there need not be exposed adhesive in both cutouts 34 and 29. An exposed cutout in either the tab or base portion 23 would suffice to maintain the tab 22 in position.

Figure 5:
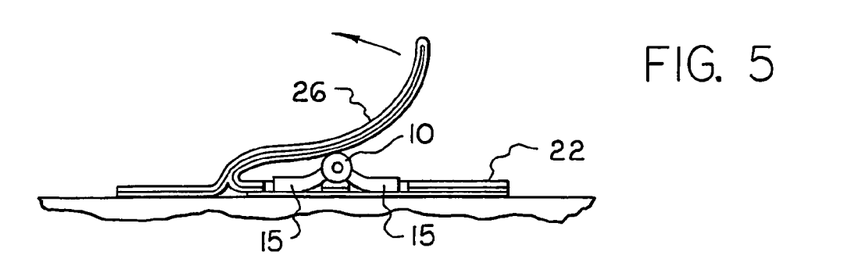
FIG. 5 is an end elevational view similar to FIG. 4 showing the tab of the winged catheter securing tape being opened.
Figure 6:
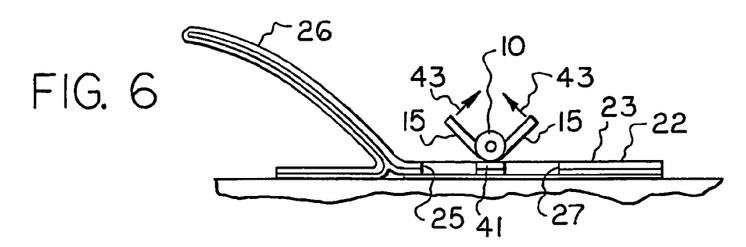
FIG. 6 is an end elevational view similar to FIG. 5 showing the tab fully opened and the winged catheter being disassembled from the securing tape.
Figure 23:
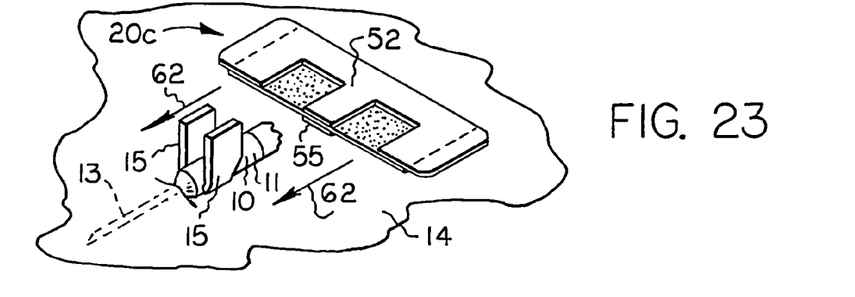
FIG. 23 is a fragmentary perspective view showing another way of mounting the winged catheter on the base of FIG. 13 after the needle of the fistula needle has been inserted through the skin.

When it is desired to remove the winged catheter 10, the procedure shown in FIGS. 5 and 6 is followed. First of all, the tab 26 is moved away from base 22, as depicted in FIG. 5. Thereafter, the wings 15 of winged catheter 10 are removed from adhesive engagement with the adhesive in cutaway portions 25 and 27 of base portion 23. Thereafter, the winged catheter 10 can be moved in the direction of arrow 42 (FIG. 3), because the tubular portion 11 of the winged catheter rests on peninsula-like portion 41 which does not have an adhesive surface. It is to be noted from FIG. 6, that after the wings 15 have been moved in the direction of arrows 43, the absence of an adhesive surface on peninsula 41 permits the winged catheter to be moved in the direction of arrow 42 (FIG. 3) without having to lift the winged catheter 10 upwardly away from base 22, as would be the case if there were adhesive on peninsula-like portion 41. Also, the lack of adhesive on peninsula 40 permits the needle to be inserted through the skin after the securing tape has been secured to the skin. In this respect the wings of the winged needle are bent to a U-configuration, as shown in FIG. 23, and held between the thumb and index finger without being attached to the securing tape, and the tip of the needle is inserted through the skin at a point substantially adjacent to the edge of the securing tape, as shown in FIG. 3, until the needle reaches its desired depth. The movement of tubular portion 11 across peninsula 41 and the portion of non-adhesive surface 40 of the tape adjacent to peninsula 41 in a direction opposite to arrow 42 can be easily effected because the surface of peninsula 41 and surface 41 do not have adhesive thereon. After the needle reaches its desired depth, the wings 15 are pressed downwardly onto tape surfaces 31 in cutouts 25 and 27.

Figures 7, 8:
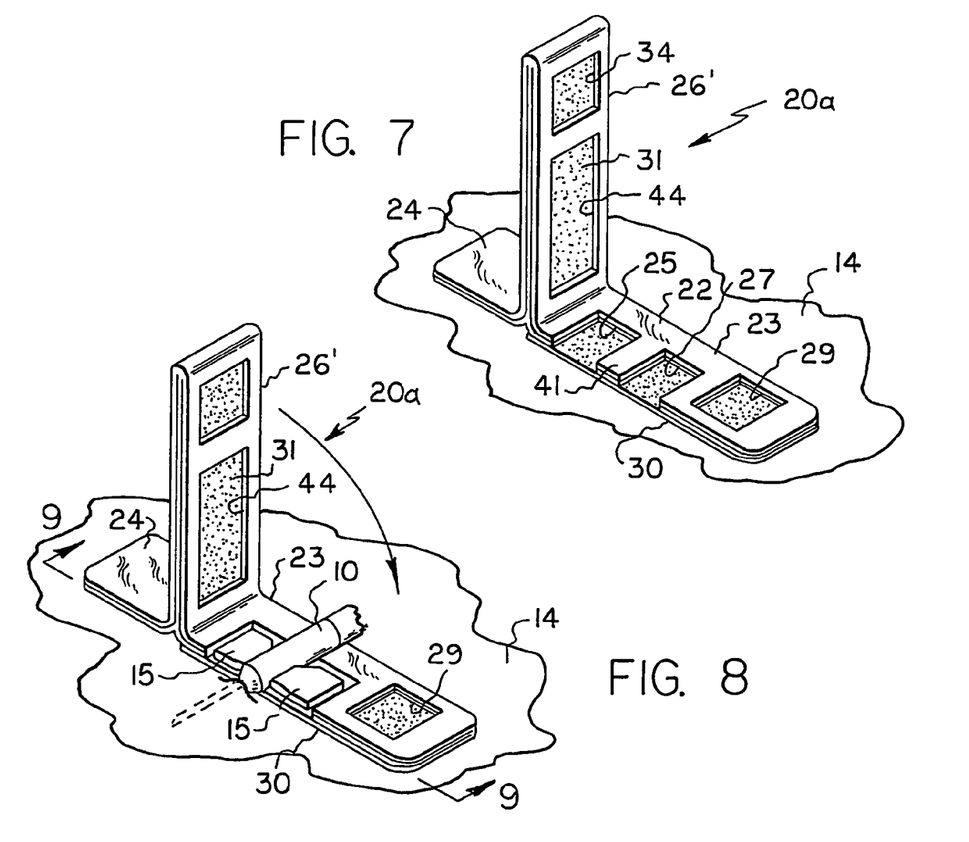
FIG. 7 is a fragmentary perspective view of another embodiment of a winged catheter securing tape mounted on a patient and having an additional window exposing adhesive on the tab for attachment to a winged catheter.
FIG. 8 is a fragmentary perspective view showing a winged catheter in the form of a fistula needle in position on the winged catheter securing tape of FIG. 7 and the tab being moved to a closed position after the needle of the winged catheter has been inserted into the patient.
Figure 9:
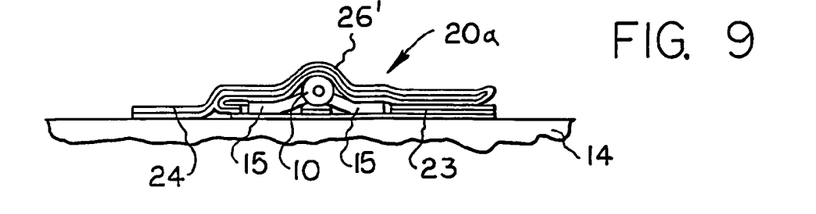
FIG. 9 is an end elevational view taken substantially in the direction of arrows 9-9 of FIG. 8 showing the tab in a fully closed position.

In FIGS. 7-9, another embodiment 20a of a winged catheter securing tape is shown. This embodiment is identical in all respects to the embodiment of FIG. 6 except for the fact that it has a cutout 44 in one layer of tab 26' which exposes the adhesive 31. The remaining structure of winged catheter securing tape 20a is identical to the embodiment of FIGS. 1-6 and will be designated by identical numerals as in FIGS. 1-6 without repeating the description thereof to which reference may be made to FIGS. 1-6. When the tab 26' (FIG. 9) is in the closed position, the adhesive 31 in cutout 44 will adhere to the portions of winged catheter 10 which it contacts, thereby more firmly holding the winged catheter 10 against movement after its needle has been inserted through the skin.

Figures 10, 11:
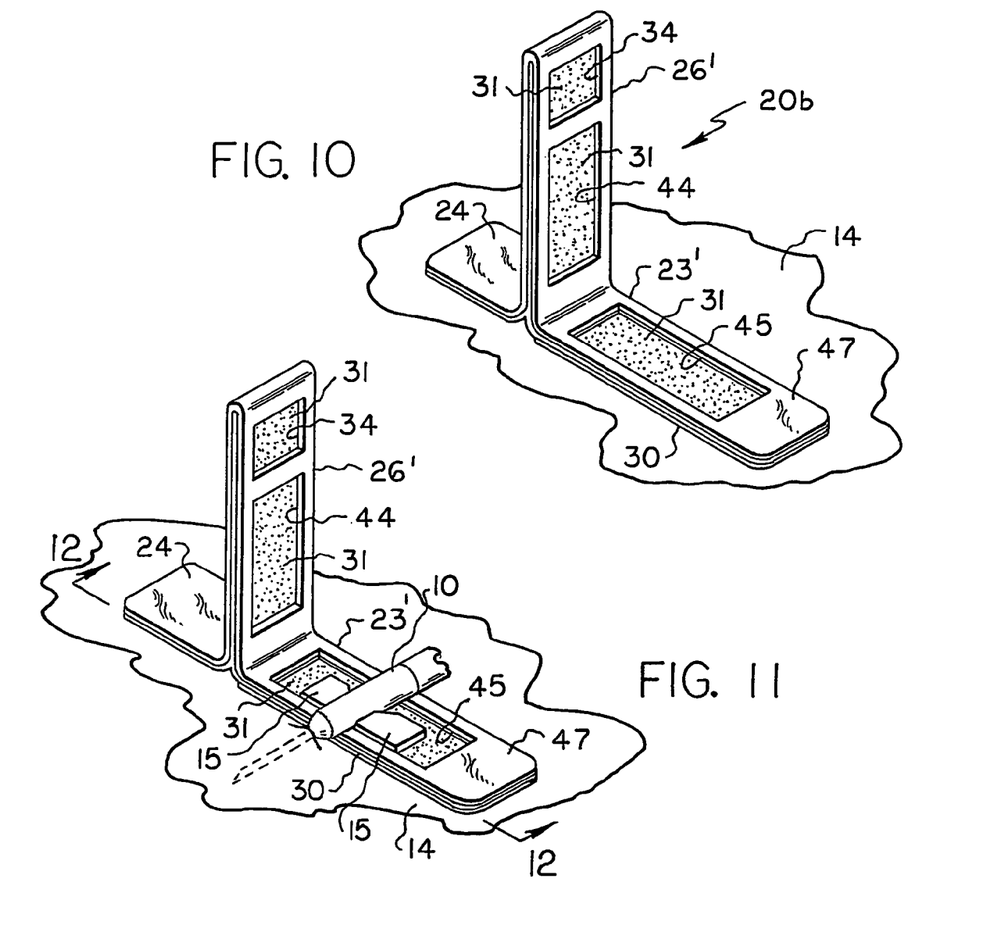
FIG. 10 is a fragmentary perspective view of still another embodiment of a winged catheter securing tape mounted on a patient.
FIG. 11 is a fragmentary perspective view showing a winged catheter in the form of a fistula needle mounted on the winged catheter securing tape of FIG. 10.
Figure 12:
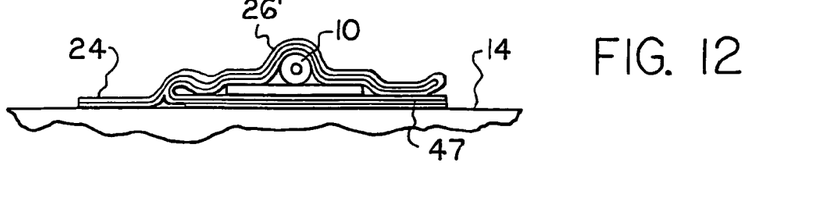
FIG. 12 is an end elevational view taken substantially in the direction of arrows 12-12 of FIG. 11 showing the tab in a closed position.

In FIGS. 10-12 another winged catheter securing tape modification 20b is shown. This embodiment differs in a number of respects from the embodiments of FIGS. 1-6 and 7-9. The tab 26' is identical to that shown in FIGS. 7-9 and will contain identical numerals without an additional description. The base portion 24 is identical to the base portions 24 of FIGS. 1-6 and 7-9. The base portion 23' differs from the base portion 23 of the preceding figures. In this respect it has an elongated cutout 45 which exposes the adhesive surface 31 of double-sided adhesive tape 30. The wings 15 are placed in cutout 45 with adhesive engagement to adhesive 31. When the tab 26' is moved to the closed position of FIG. 12, the adhesive 31 in cutout 34 will engage the non-adhesive surface portion 47 at the outer end of base portion 23' to retain the tab 26' in its position of FIG. 12. Also, the adhesive 31 in cutout 44 will function in the same manner as described above relative to the embodiment of FIGS. 7-9. It will be appreciated that, if desired, a non-adhesive strip may be placed in cutout 45 to function in the same manner as peninsula-like structure 41 of FIGS. 1-6 and 7-9.

In FIGS. 13-18 a winged catheter securing tape base 20c is shown. The base 20c is formed from a strip of non-adhesive tape 49 having end portions 50 and cutouts 51 therein with a peninsula-like portion 52 therebetween. A double-sided tape 53 is adhesively secured to the lower surface or underside 56 of tape 49 so that an adhesive surface faces upwardly through cutouts 51 after double-sided adhesive tape 53 has been assembled with non-adhesive tape 49. Two pieces of release paper 54 cover the lower surface of double-sided tape 53, and a strip 55 of non-adhesive material is secured to the underside of double-sided tape 53. The end portions 50 of non-adhesive tape protrude beyond double-sided tape 53 (FIG. 13A). It will be appreciated that double-sided tape 53 may be identical to double-sided tape 30 described above in FIG. 1 or it may be a type of adhesive film which is not actually a double-sided tape, but consists of an adhesive stratum. It will be appreciated that the adhesive stratum and the double-sided adhesive tapes 30 and 53, are essentially interchangeable and will be so considered relative to all embodiments of the present invention.

The winged catheter securing tape 20c functions in the following manner: After the two pieces of release paper 54 are removed, the base 49 is applied to the patient 14. Thereafter, the wings 15 of the winged catheter are adhered to the portions of adhesive 53 which extend upwardly through cutouts 51 after the needle 13 has been inserted through the skin of the patient. Thereafter, an independent strip of adhesive tape 57 is overlaid on the base 49, as depicted in FIG. 15, with the ends of the independent strip 57 extending beyond the securing tape 20c onto the skin.

Figure 17:
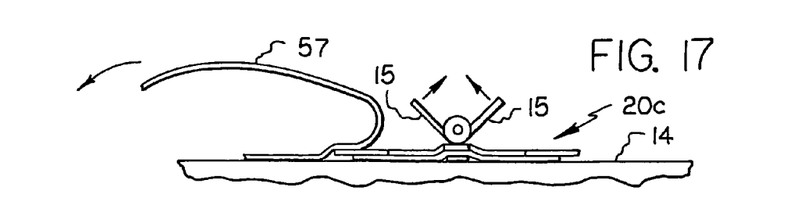
FIG. 17 is an end elevational view showing the overlying tape being removed and the winged catheter being removed from the base.

In order to remove the winged catheter from the patient, the first step is to remove the adhesive tape 57 (FIG. 17) and thereafter lift the wings 15 away from adhesive securement with base 20c, as also shown in FIG. 17. Thereafter, the needle 13 can be withdrawn from the patient by pulling the needle in the direction of arrow 42 of FIG. 3, considering that there is no adhesive securement between tubular portion 11 of the winged catheter and the base 20c because of the presence of peninsula-like portion 52. Thereafter, the base 20c can be removed from the patient very easily because the extreme ends 50 of non-adhesive tape 49 extend beyond the double-sided adhesive tape 53 so that such ends may be easily grasped. While member 49 is shown as being a non-adhesive tape of the type having a non-adhesive surface, it will be appreciated that an adhesive tape can also be used with cutouts 57 provided that the adhesive surface is placed against the double-sided tape 53. If it is desired to have non-adhesive ends such as 50 (FIG. 13A) when using an adhesive tape, the adhesive lower surface can terminate short of non-adhesive ends 50.

The base 20c can also be removed from the skin without removing tape 57 from base 20c. In this respect, the ends of tape 57 need merely be pulled sufficiently away from the skin to expose ends 50, and thereafter the ends 50 can be pulled away from the skin while tape 57 is still in overlying relationship to base 20c, with the wings of the winged catheter 10 sandwiched between base 20c and tape 57.

Figures 13, 13A, 14, 15, 16, 18:
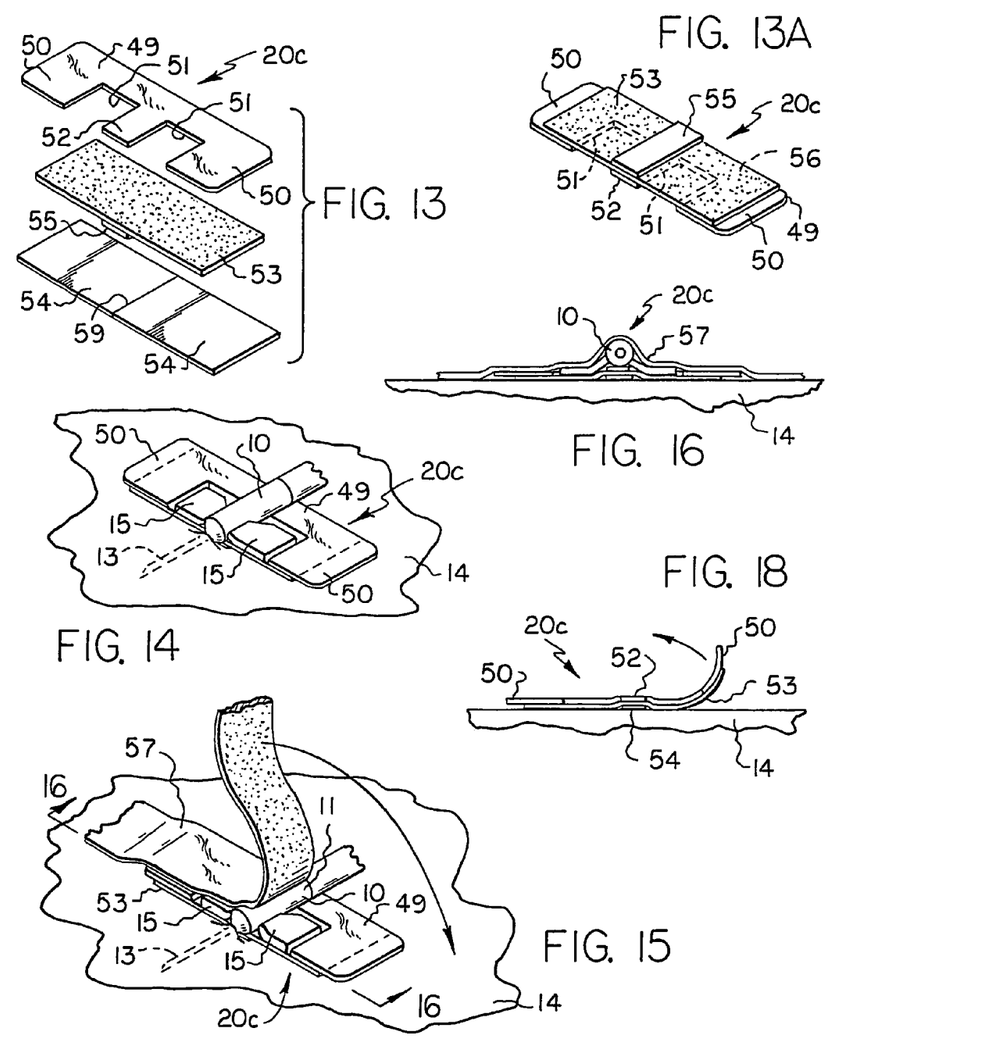
FIG. 13 is an exploded fragmentary perspective view of a winged catheter securing tape base which does not have an attached tab and which is also designed for one-handed operation by a dialysis patient who will have the securing tape mounted on his arm.
FIG. 13A is a perspective view of the base of FIG. 13 showing the underside thereof.
FIG. 14 is a fragmentary perspective view of the winged catheter securing tape base of FIG. 13 mounted on a patient and with a winged catheter in the form of a fistula needle mounted on the securing tape.
FIG. 15 is a fragmentary perspective view showing how a separate overlying piece of tape is applied to the winged catheter securing tape base having the winged catheter mounted thereon.
FIG. 16 is an end elevational view taken substantially in the direction of arrows 16-16 of FIG. 15 showing the winged catheter securing tape with an overlying tape in a fully closed position.
FIG. 18 is an end elevational view showing the securing tape base being removed from the skin of the patient.
Figures 19, 19A, 20, 21, 21A, 22:
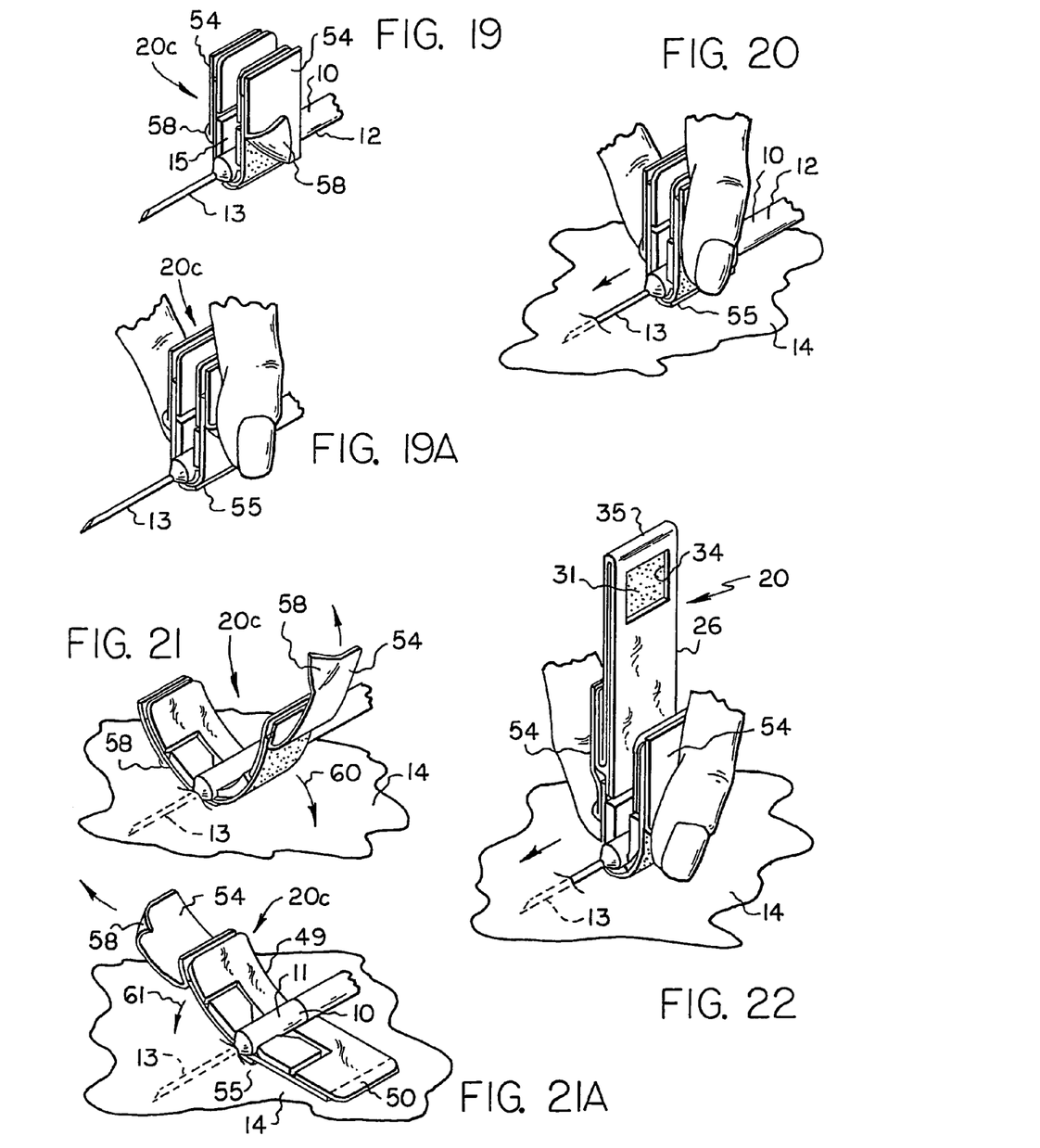
FIG. 19 is a fragmentary perspective view showing the base of FIG. 13 with a winged catheter in the form of a fistula needle mounted thereon and the configuration which it assumes when it is being held by a person preparatory to inserting the needle through the skin.
FIG. 19A is a fragmentary perspective view showing the base of FIG. 19 being held by a person.
FIG. 20 is a fragmentary perspective view showing the base of FIG. 19 being held by a person and the needle being inserted through the skin.
FIG. 21 is a fragmentary perspective view showing the base being pressed down onto the skin after the needle has been inserted and also showing the release paper being removed.
FIG. 21A is a fragmentary perspective view of the final step of removing the release paper and pressing the base onto the skin.
FIG. 22 is a fragmentary perspective view similar to FIG. 19 but showing the needle of the winged catheter on the securing tape of FIG. 2 being inserted through the skin.

In FIGS. 19-21A the steps are shown whereby the winged catheter securing base of FIGS. 13-18 may be installed onto a patient using one hand. This is done in cases wherein the winged needle has to be applied to the arm of a person working by himself. This procedure includes using two hands to apply the winged catheter 10 to the base 20c with wings 15 in position, as shown in FIG. 14. Thereafter, using both hands, the release paper 54 is bent up as shown with their corners 58 in the position shown in FIG. 19. In this respect, as noted above, when the release paper pieces 54 are initially installed, they are separated along line 59 (FIG. 13). Thereafter, a person grasps the winged catheter securing base 20c between the thumb and index finger while pressing on turned-up tabs 58, after the winged catheter securing tape has been folded into the U-configuration shown in FIGS. 19 and 19A. Of course, after the winged catheter 10 has been applied to the base, the winged catheter securing tape 20c can be folded into the U-shape before the tabs 58 are turned up. The next step is to insert needle 13 through the skin of patient 14, as depicted in FIG. 20. After the needle 13 has been inserted through the skin to the desired depth, the central portion of base 20c is pressed down onto the skin to adhesively secure the portions of the base on opposite sides of strip 53 against movement, and this is followed by removing release paper 54 and pressing one side of the base onto the skin, as depicted by arrow 60. Thereafter, the other piece of release paper 54 is removed followed by pressing the other portion of the base onto the skin as depicted by arrow 61 (FIG. 21A).

The winged catheter securing base 20c of FIG. 13 can be removed from its fully mounted position with one-handed operation in the following manner: The ends 50 of the base are not adhesively secured to the skin. Therefore, the ends can be lifted up with one hand and the adjacent portions of the base can be detached from adhesive relationship with the skin, one side at a time. Thereafter, the base is manipulated into a U-shaped configuration, and the needle 13 is withdrawn from the patient in a straight line direction, as depicted by arrow 42 of FIG. 3. This is facilitated by the fact that the non-adhesive strip 55 underlies the portion 11 of the winged needle to thereby permit direct line removal in the direction 42 (FIG. 3). If there was an adhesive securement underneath tubular portion 11, the winged catheter would have to be bent away from the patient, thereby tending to move needle 13 upwardly away from the patient while it was still embedded in the patient.

In FIG. 22 it is shown how a winged catheter securing tape, such as shown in FIGS. 1-6, can be applied to a patient by one-handed operation by moving the parts to the position shown in FIG. 22, by following the steps essentially described above in FIGS. 19-21A. The only difference between the winged catheter securing tape shown in FIG. 22 and that shown in FIG. 1 is that the embodiment shown in FIG. 22 utilizes two pieces of release paper 54 rather than the one piece of release paper 39 shown in FIG. 1. After needle 13 has been inserted to the required depth, the steps described above relative to FIGS. 19-21A are followed for completing the insertion. Also the steps described above can be followed for removing the needle from the patient.

Figure 24:
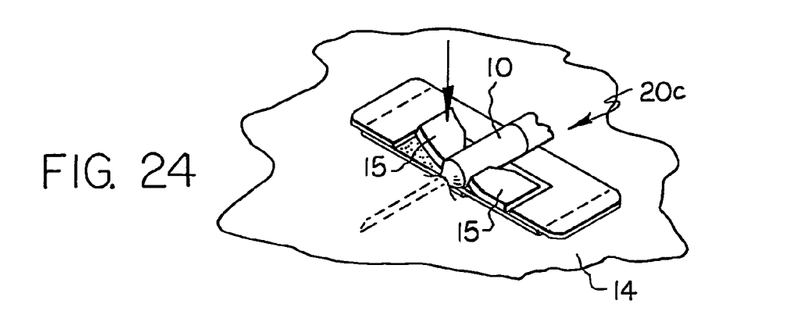
FIG. 24 is a fragmentary perspective view showing the winged catheter being secured to the base after the base has been moved into position under it and after the needle has been inserted through the skin.

In FIGS. 23 and 24 a procedure is depicted for mounting a winged catheter 10 onto a base 20c after the needle 13 has been inserted through the skin 14 to the proper depth. In this respect, the needle is inserted by folding the wings 15 up as shown to grasp opposite sides thereof and inserting the needle 13 through the skin to the proper depth. Thereafter, while the wings 15 are held in the position shown in FIG. 23 with the tubular portion 11 away from the skin, the winged catheter securing tape base 20c, with the release paper 54 removed from the central portion thereof proximate non-adhesive strip 55, is slid in the direction of arrows 62 with the peninsula-like portion 52 underlying the tubular portion 11 of the winged needle. When the winged catheter securing tape 20c reaches the proper position, the release paper 54 is fully removed, and the base 20c is pressed downwardly onto the skin 14 to provide adhesive securement therewith. Thereafter, the wings 15 are pressed downwardly onto the securing tape, as depicted in FIG. 24. The existence of non-adhesive strip 55 permits the securing tape 20c to be slid in the direction 62 while the adjacent adhesive portions of the undersurface are held slightly away from the skin.

Figures 25, 26, 27:
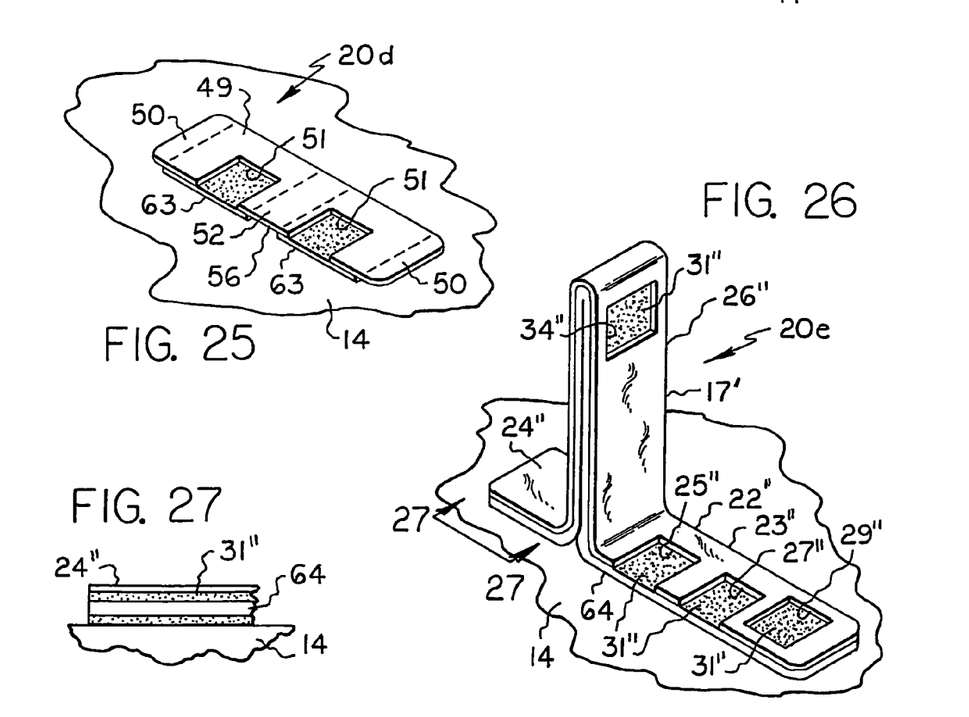
FIG. 25 is a fragmentary perspective view of another embodiment of a winged catheter securing tape base which is a variation of the base of FIG. 13.
FIG. 26 is a fragmentary perspective view of another embodiment wherein a winged catheter securing tape is produced by combining a cutout ribbon with a double sided tape.
FIG. 27 is a fragmentary view taken substantially in the direction of arrows 27-27 of FIG. 26.
Figures 28, 29, 30:
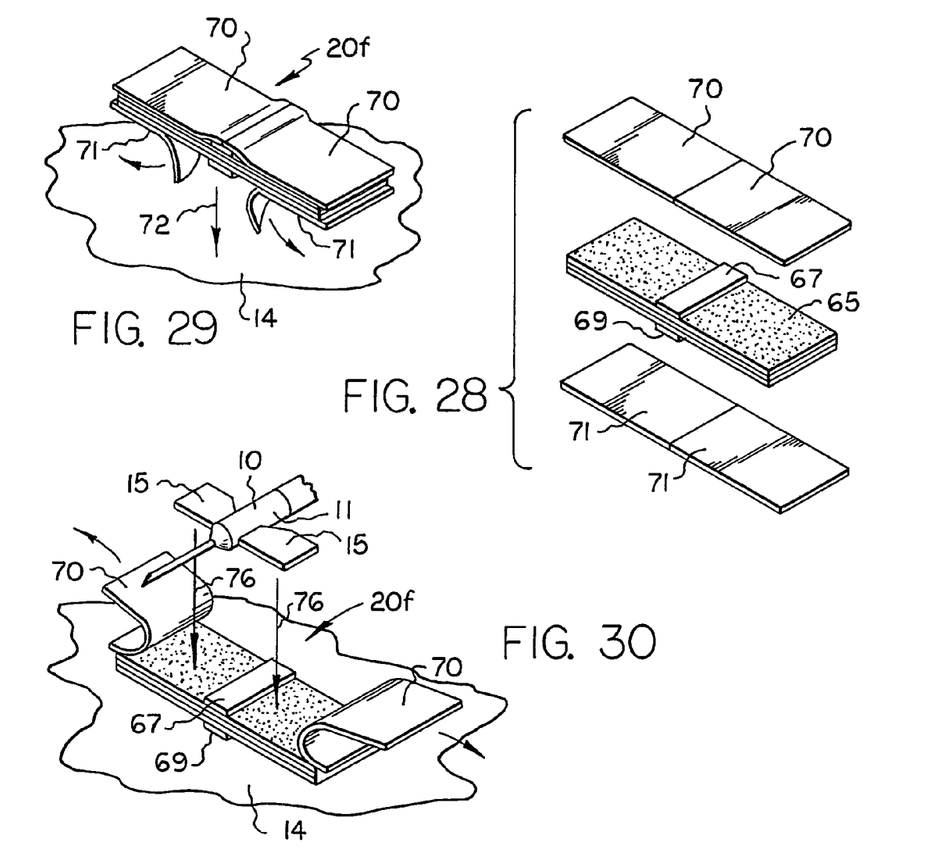
FIG. 28 is an exploded view of still another embodiment of a winged catheter securing tape base.
FIG. 29 is a fragmentary view showing the base of FIG. 28 overlying a patient's skin and in the process of having the release paper removed.
FIG. 30 is a fragmentary perspective view showing the base of FIG. 29 secured to the patient's skin and the release paper being removed from its top to expose the adhesive and the winged catheter being applied to the exposed adhesive.
Figure 31:
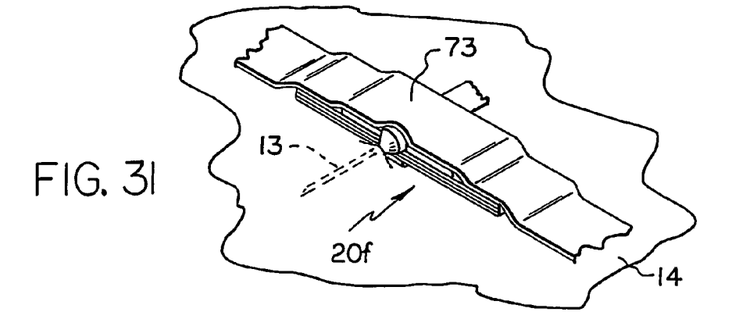
FIG. 31 is a fragmentary perspective view showing the winged catheter fully mounted on the patient's skin with a ribbon attached to the top thereof.

Another embodiment 20d which is similar to the securing tape 20c is shown in FIG. 25. This embodiment includes a non-adhesive tape 49 as described above relative to FIG. 13. However, it does not use a full length of adhesive material such as described above at 53 relative to FIG. 13. Instead it uses two spaced pieces 63 of adhesive material placed on the underside of tape 49 so as to provide adhesive surfaces within cutaways 51. A non-adhesive surface 56 is located between adhesive pieces 54. Thus, this embodiment does not utilize an extra strip of non-adhesive material, such as 55 (FIG. 13A) underneath peninsula-like portion 52.

In FIGS. 26 and 27 a still further embodiment of the present invention is shown. This embodiment 20e includes a non-adhesive tape 17' which is similar in all respects to adhesive tape 17 of FIG. 1 except that it does not have an adhesive undersurface. This non-adhesive tape 17' is mounted on a double-sided tape 64 such that the double-sided tape underlies base portions 23" and 24" of base 22" and also underlies the sides of tab 26" so that when tab 26" is formed, the two sides thereof adhere to each other. Furthermore, the adhesive surface 31" protrudes through cutouts 34", 25", 27", and 29".

In FIGS. 28-31 yet another winged catheter securing tape 20f is shown which comprises a base of double-sided tape 65 having a non-adhesive strip 67 adhesively secured to the upper surface thereof and a strip of non-adhesive tape 69 secured to the undersurface thereof in opposition to tape 67. Two release paper sections 70 are applied to the upper surface of double-sided tape 65 and two release paper sections 71 are applied to the lower surface of double-sided tape 65. To apply the winged catheter securing tape 20f to the patient's skin 14, the two pieces of release paper 71 are pulled away from the undersurface and the tape is pressed down onto the skin as depicted by arrow 72. Thereafter, the release paper 70 is removed from the upper surface of the winged catheter securing tape 20f. The needle 13 is then inserted through the skin and the wings 15 are pressed down onto the upper surface in the direction of arrows 76 with the central tubular portion 11 thereof overlying non-adhesive surface 67. Thereafter, a separate piece of tape 73 is placed in overlying relationship to winged catheter securing tape 20f with the winged needle 10 mounted thereon. The tape 76 may be adhesive or non-adhesive tape. Adhesive tape is preferable so that its ends may extend beyond tape 65 and adhere to the skin. As noted above, the double-sided adhesive tape 65 can be replaced by a type of tape which comprises a stratum of adhesive which has an adhesive surface on opposite sides thereof without being applied to a tape therebetween.

Figures 32, 33:
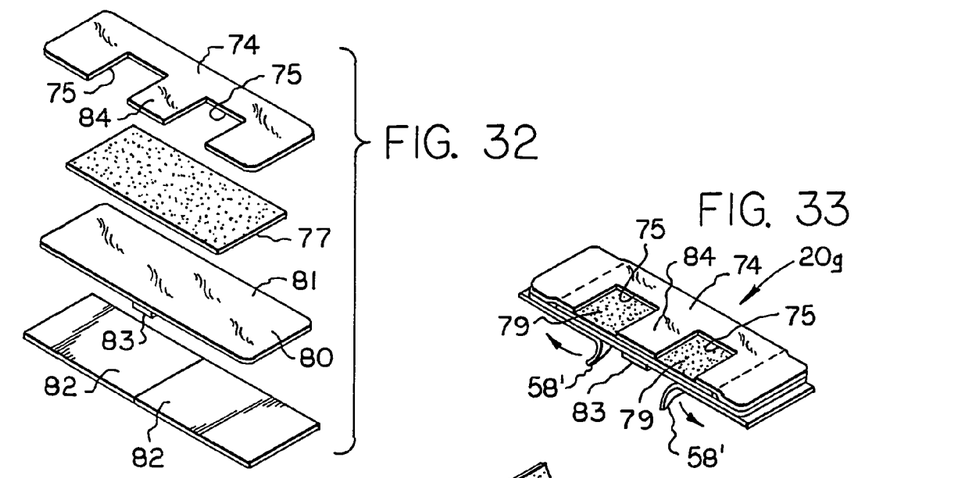
FIG. 32 is a perspective exploded view of another embodiment of a winged catheter securing tape base which does not have an attached tab and which is designed for one-handed operation by a dialysis patient who will have the securing tape mounted on his arm.
FIG. 33 is a perspective view of the winged catheter securing tape of FIG. 32 in assembled condition and which is being partially disassembled.
Figures 34, 35, 36:
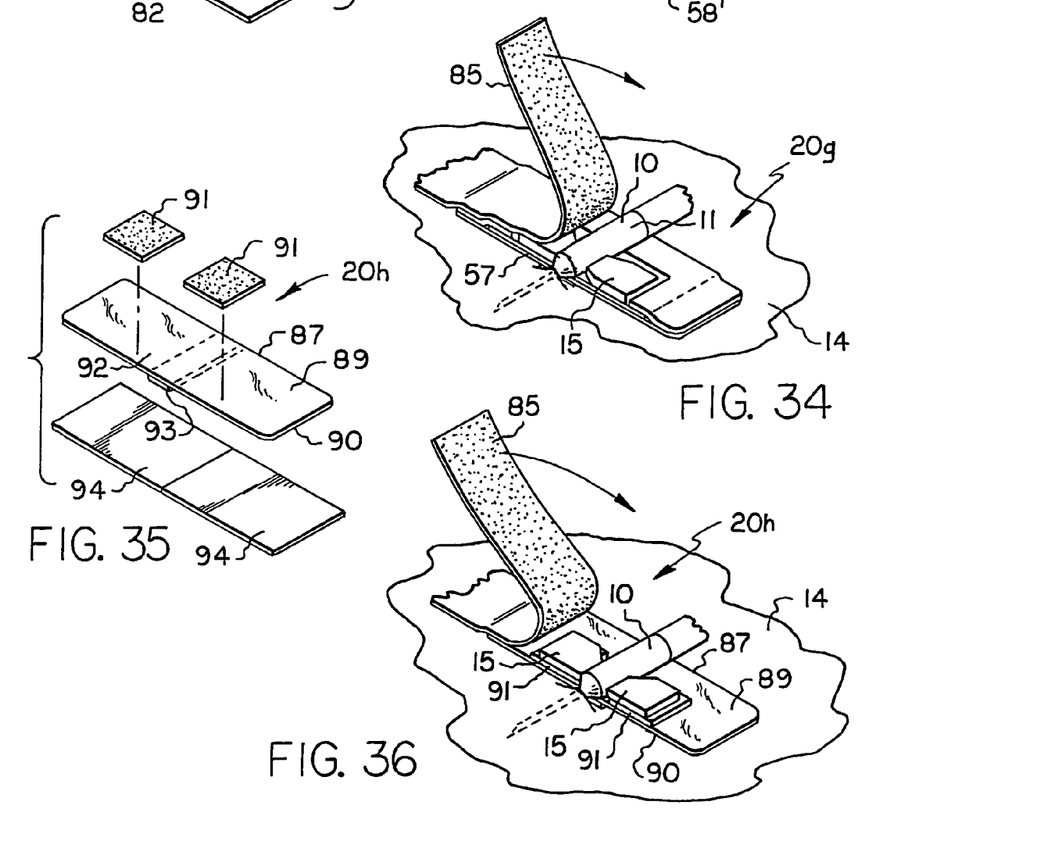
FIG. 34 is a fragmentary perspective view of the winged catheter securing tape base of FIG. 33 adhesively secured to a patient's skin with the needle of the fistula needle inserted through the patient's skin and with a tape being applied over the winged catheter.
FIG. 35 is an exploded view of another embodiment of a winged catheter securing tape base which does not have an attached tab.
FIG. 36 is a fragmentary view of an assembled winged catheter securing tape of FIG. 35 mounted on a patient's skin with the needle inserted through the skin and an overlying tape being applied to the base.

In FIGS. 32-34 another embodiment 20g of a winged catheter securing tape is shown which is capable of being applied by one hand, as is sometimes necessary by a dialysis patient. This procedure was described above relative to FIGS. 19-21A. The embodiment 20g is a variation of the embodiment of FIGS. 13-18. In this respect, the securing tape 20g includes a tape 74 having cutouts 75 therein. A double-sided adhesive member 77 is placed in underlying relationship to tape 74 so that portions 79 of tape 77 are exposed through cutaway portions 75. An adhesive tape 80 has its non-adhesive surface 81 adhesively secured to the underside of member 77. Two pieces of release paper 82 are applied to the underside of adhesive tape 80 which has a strip 83 with a non-adhesive surface extending downwardly underlying peninsula-like portion 84 of tape 74. One of the initial steps in applying the winged catheter securing tape to the skin 14 is to form tabs 58' which correspond to tabs 58 of FIG. 19. Thereafter, the procedure described above in FIGS. 19-21A is followed to apply the winged catheter 10 to the patient. This includes the step of applying an adhesive tape 85 in overlying relationship to the installed winged catheter securing tape 20g, as depicted in FIG. 34, with the ends of tape 85 being adhesively secured to the skin.

Figures 37, 38, 39:
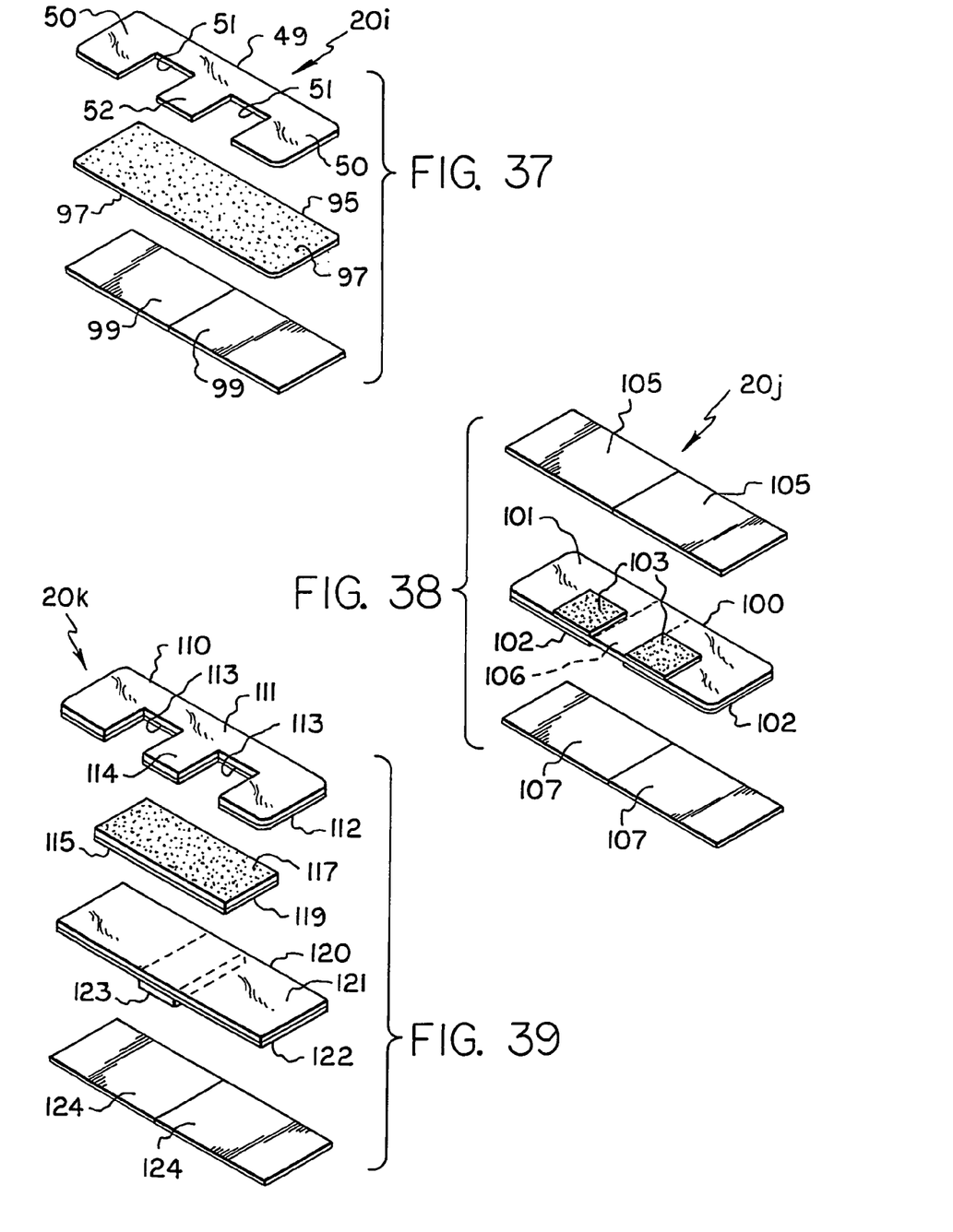
FIG. 37 is an exploded view of a winged catheter securing tape base which is similar to FIG. 13 but which utilizes a stratum of adhesive instead of double-sided adhesive tape.
FIG. 38 is an exploded view of still another embodiment of a winged catheter securing tape base which has roll-coated adhesive surfaces on both the upper and lower surfaces thereof.
FIG. 39 is an exploded view of still another embodiment of a winged catheter securing tape base which is fabricated of a plurality of pieces of adhesive tape.

Another winged catheter securing tape embodiment 20h is shown in FIGS. 35 and 36. This embodiment comprises an adhesive tape 87 having a non-adhesive surface 89 and an adhesive surface 90. Two spaced patches 91 of adhesive material are applied to the non-adhesive surface 89 with a non-adhesive space 92 therebetween which in essence corresponds to peninsula-like portion, such as 84, shown above relative to FIG. 33 and other figures. A non-adhesive strip 93 is adhesively attached to the adhesive undersurface 90 of tape 87. The winged catheter 10 has its wings 15 attached to spaced adhesive patches 91, as shown in FIG. 36. After the two pieces 94 of release paper are removed from the adhesive undersurface 90, the winged catheter securing tape 20h can be applied to the skin 14 of the patient, and will occupy a final position as shown in FIG. 36. The securing tape 20h is applied to the skin by the method shown in FIGS. 19-21A, or it can be applied in the manner such as shown in FIGS. 23 and 24. In FIG. 37 an embodiment 20i of a securing tape is shown which includes a non-adhesive type of tape 49 as described in detail above relative to FIG. 13. This mounts on a tape film or stratum 95 which has adhesive surfaces 97 on opposite sides thereof. This was alluded to above as a member which could function in the same manner as the double-sided tape 53 described above relative to FIG. 13. Two pieces of release paper 99 are applied to the undersurface 97 and are removed prior to installation in the manner described above relative to FIGS. 19-21A. While not shown in FIG. 37, it can have a non-adhesive strip like 55 of FIG. 13 on its undersurface. Thus, the only difference between FIG. 37 and FIG. 13 is that the latter uses double-sided adhesive type whereas FIG. 37 utilizes an adhesive film or stratum having adhesive on opposite sides thereof.

In FIG. 38 another embodiment 20j of a winged catheter securing tape is shown. This embodiment includes a non-adhesive tape 100 having an upper non-adhesive surface 101 and a lower non-adhesive surface. Two spaced adhesive areas 102 are located on the lower surface. A non-adhesive strip 106 of the lower surface is located between adhesive areas 102. In addition, it has two spaced adhesive areas 103 located on upper surface 101 with a non-adhesive portion 104 therebetween. The adhesive surfaces 102 and 103 are coated on said upper surface by roll coating or spraying or any other suitable coating method other than by application of separate distinct patches of tape or adhesive stratum. Release paper pieces 105 cover the non-adhesive surface 101 by adhering to adhesive patches 103. Two pieces of release paper 107 cover adhesive surfaces 102.

In FIG. 39 another winged catheter securing tape embodiment 20k is shown which is fabricated from a plurality of pieces of one-sided adhesive tape. In this respect, one-sided adhesive tape member 110 has a non-adhesive surface 111 and an adhesive surface 112. It also has cutouts 113 therein with a peninsula-like member 114 therebetween. The adhesive 112 is across the entire lower surface. A second piece of one-sided adhesive tape 115 has an adhesive upper surface 117 and a non-adhesive lower surface 119. Adhesive tape 115 has its adhesive surface 117 adhered to adhesive surface 112 such that portions of its adhesive upper surface 117 are located within cutouts 113 with the adhesive facing upwardly so as to adhesively secure the wings 115 thereto as described above relative to other embodiments. A third piece 120 of one-sided adhesive tape has an upper non-adhesive surface 121 and an adhesive surface 122. One-sided adhesive tape 120 is placed in underlying relationship to one-sided adhesive tape 110 so that it is adhesively secured thereto. The securement would be at all sides around tape 117. A strip of material 123 is adhesively secured to adhesive surface 122 so that it underlies peninsula-like member 114 and extends all the way to the rear edge of one-sided tape 120. Two pieces 124 of release paper are adhesively secured to the adhesive surface 122. A modification of FIG. 39 can use a piece of two-sided adhesive rather than one-sided adhesive tape 115. This modification would provide adhesive contact to the non-adhesive surface 121 of tape 120. The winged catheter securing tape 20k can function in the same manner described above relative to FIGS. 19-21 A.

Figure 40:
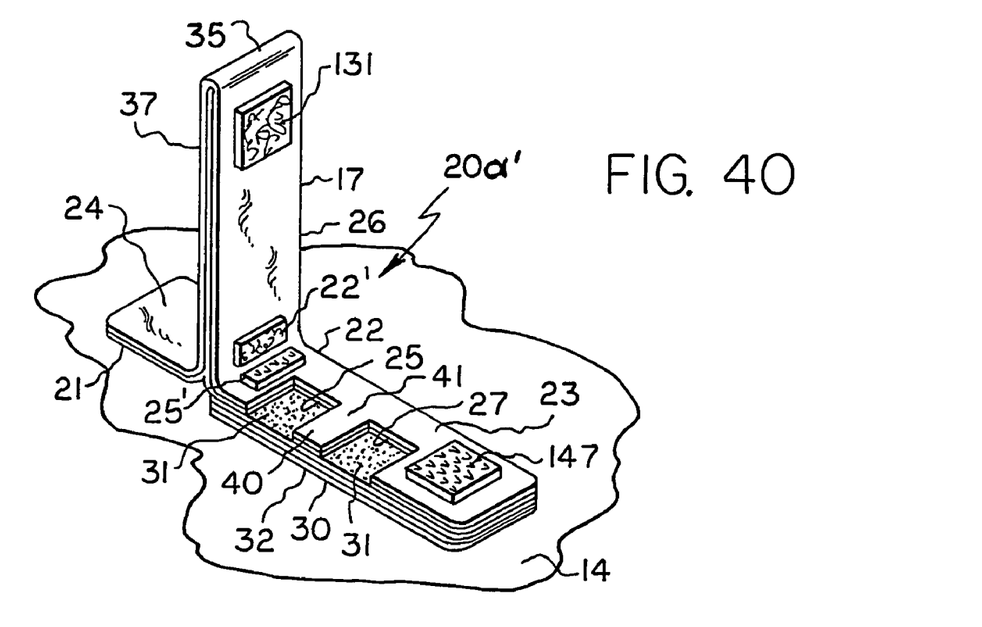
FIG. 40 is a perspective view of still another embodiment of a winged catheter securing tape which is similar to FIG. 2 but uses hook and pile fabric to secure the tab to the base.
Figure 41:
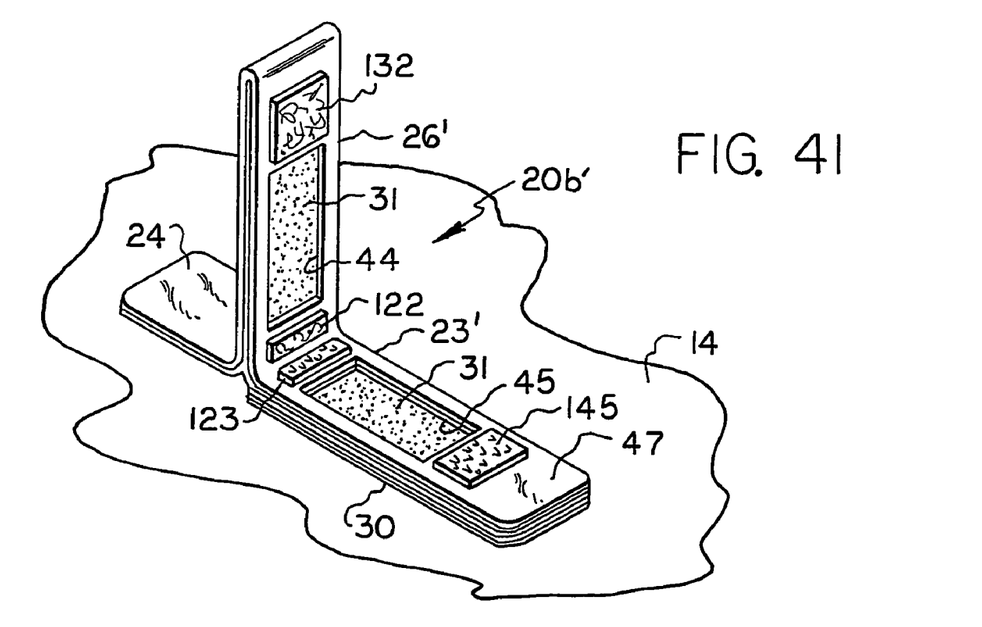
FIG. 41 is a perspective view of still another embodiment of a winged catheter securing tape which is similar to the tape of FIG. 9 but uses hook and pile fabric to secure the tab to the base.

FIGS. 40 and 41 are modifications of FIGS. 7 and 10, respectively. All numerals on FIGS. 40 and 41 which are identical to the numerals on FIGS. 2 and 10, respectively, designate like elements of structure and therefore will not be described again. FIGS. 40 and 41 differ from FIGS. 7 and 10, respectively, in that the tabs are secured to the bases by hook and pile fabric rather than by adhesive connections. In this respect, in FIG. 40 the outer end of tab 17 has a patch of pile fabric 131 secured thereto, and a patch of hook fabric 147 is secured to the outer end of base portion 23. In addition, a piece of pile fabric 22' is secured proximate the fixed end of tab 17 and a piece of hook fabric 25' is secured on base portion 23 proximate tab 17. When the tab 17 is closed, as shown in FIG. 4, pile fabric 22' will mate with hook fabric 25', and pile fabric 131 will mate with hook fabric 147.

As noted above, the embodiment of FIG. 41 also utilizes hook and pile fabric to secure tab 26' to base portion 23'. In this respect a patch of pile fabric 132 is secured proximate the free end of tab 26' and a patch 145 of hook fabric is secured proximate the outer end of base 23'. In addition, a patch of pile fabric 122 is secured to tab 26' proximate base 23' and a patch 123 of hook fabric is secured to base 23' proximate tab 26'. When the tab 26' is engaged with base 23', as shown in FIG. 12, the pile fabric 122 will mesh with hook fabric 123 and the pile fabric 132 will mesh with hook fabric 145.

Preferably the hook and pile fabrics which are utilized in FIGS. 40 and 41 are a product of Velcro Corporation sold under the trademark ULTRA MATE. The specific designation of this product is HTH-8300709915. The advantage of using this particular type of hook and pile fabric is that it is of a lower height than the normal hook and pile fabric which was previously on the market, and in effect, it is approximately 1/10th the height of the previous hook and pile fabric.

Figure 42:
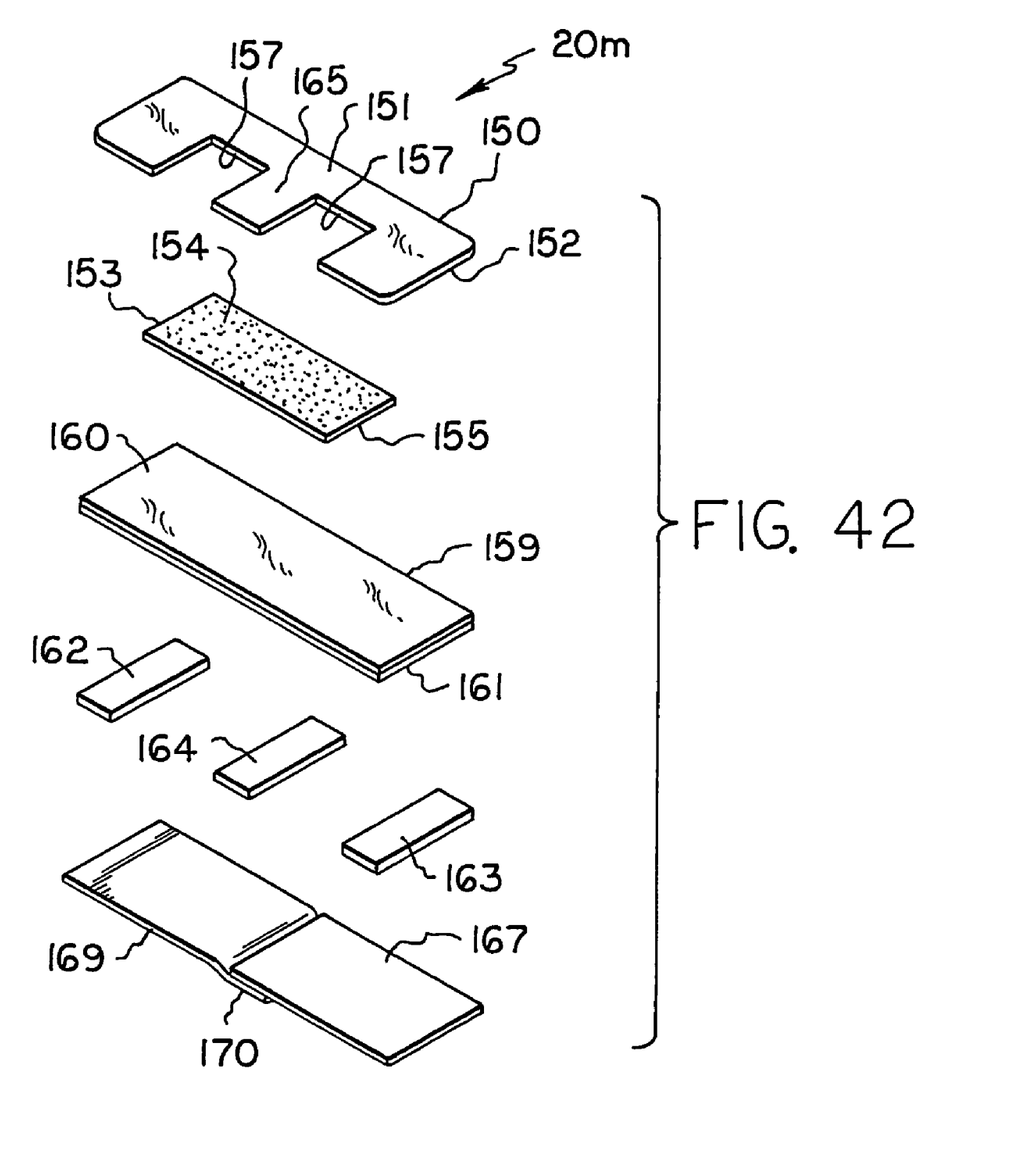
FIG. 42 is an exploded view of still another embodiment of the winged catheter securing tape of the present invention.

In FIG. 42 another winged catheter securing tape embodiment 20m is shown in exploded form. It includes a one-sided tape member 150 having a non-adhesive surface 151 and an adhesive surface 152. An adhesive tape 153 having an adhesive surface 154 and an non-adhesive surface 155 is adhesively secured to the adhesive surface 152 so that adhesive is exposed through cutouts 157. Alternately if desired, member 153 can be double-sided adhesive or two small patches of one-sided adhesive tape or two small patches of double-sided adhesive tape. Member 153 should just extend slightly beyond the cutouts sufficiently so that its edges adhere to tape 150. An adhesive tape 159 is adhesively secured to tape 150. In this respect it has a non-adhesive surface 160 and an adhesive surface 161. Non-adhesive members 162, 163, and 164 are adhesively secured to adhesive surface 161 of adhesive tape 159. In this respect members 162 and 163 are adhesively secured at the ends of member 159 and member 164 is adhesively secured to the central portion of member 159 underneath peninsula-like portion 165 of tape 150. Members 162, 163, and 164 extend for the entire width of member 159.

Preferably member 164 should be the same width as peninsula-like portion 165. Release paper 167 is adhesively secured to the portion of adhesive 161 between members 163 and 164. Release paper 169 is adhesively secured to the portion of adhesive surface 161 between members 162 and 164. The end 170 of release paper 169 overlies a portion of release paper 167 so that it can be grasped easily for removal. Members 162 and 163 essentially block the adhesive at the end portions of adhesive surface 161 so that the ends of adhesive tape 159 are not adhesively secured to the skin so that the ends can readily be grasped for removal from the skin.

While not shown in FIGS. 1-12, it will be appreciated that these embodiments may have a strip such as 55 of FIG. 13 or equivalent non-adhesive strips such as 106 of FIG. 38 on their undersurfaces.

It is to be noted that in all figures where the fistula needle is actually in operating position for dialysis, the conical nose is in the required abutting relationship with the patient's skin to seal the skin against blood flow through the area of skin penetration.

It is also to be noted that while the release paper is shown in a central overlapping position only in the embodiment of FIG. 42, this overlapping relationship can be effected in all other embodiments where release paper is shown.

While preferred embodiments of the present invention have been disclosed, it will be appreciated that it is not limited thereto but may be otherwise embodied within the scope of the following claims.

I claim:

1. A laminated winged catheter securing tape comprising:
a tape base having an upper surface and a lower surface, said tape base defining at least one cutout extending from said upper surface through to said lower surface to form an opening therethrough; and,
an adhesive member having an upper side and a lower side, wherein said upper side is adhesively attached to at least part of said lower surface of said tape base; and,
wherein an adhesive surface is exposed in at least one of said at least one cutouts;
wherein each of said upper surface and said lower surface of said tape base is a nonadhesive surface and said at least one cutout is two cutouts, each of said two cutouts formed by the edge of said tape base and having a nonadhesive segment positioned between said two cutouts; and,
wherein each of said upper side and said lower side of said adhesive member are adhesive sides and at least part of said upper adhesive side is exposed in each of said two cutouts; and,
further comprising a nonadhesive strip positioned on said lower adhesive side and at least one release paper covering said lower side.

2. The laminated winged catheter securing tape as recited in claim 1 wherein said nonadhesive strip is aligned under said nonadhesive segment.

3. The laminated winged catheter securing tape as recited in claim 1 wherein said at least one release paper is two release papers.

4. The laminated winged catheter securing tape as recited in claim 1 wherein each of the end portions of said tape base protrude beyond each of the ends of said adhesive member.

5. The laminated winged catheter securing tape as recited in claim 1 wherein said adhesive member is a double-sided tape.

6. The laminated winged catheter securing tape as recited in claim 1 wherein said adhesive member is an adhesive stratum having an adhesive upper side and an adhesive lower side.

7. The laminated winged catheter securing tape as recited in claim 1 further comprising an overlay tape having an upper and a lower surface, wherein said lower side of said overlay tape is adhesive and the ends of said overlay tape extend beyond the ends of said tape base;
   wherein said overlay tape is adhesively attached to at least part of said upper surface of said tape base.

8. The laminated winged securing tape as recited in claim 1 wherein said at least one release paper is two release papers.

9. A laminated winged catheter securing tape comprising:
   a tape base having an upper surface and a lower surface, said tape base defining at least one cutout extending from said upper surface through to said lower surface to form an opening therethrough; and,
   an adhesive member having an upper side and a lower side, wherein said upper side is adhesively attached to at least part of said lower surface of said tape base; and,
   wherein an adhesive surface is exposed in at least one of said at least one cutouts;
   wherein each of said upper surface and said lower surface of said tape base is a nonadhesive surface and said at least one cutout is two cutouts, each of said two cutouts formed by the edge of said tape base and having a nonadhesive segment positioned between said two cutouts; and,
   wherein each of said upper side and said lower side of said adhesive member are adhesive sides and at least part of said upper adhesive side is exposed in each of said two cutouts; and,
   further comprising a strip of tape having one adhesive side and one nonadhesive side wherein said nonadhesive side of said tape strip is adhesively attached to said lower side of said adhesive member, a nonadhesive strip positioned on said lower adhesive side of said tape strip and two release papers attached to said adhesive side of said adhesive tape.

10. The laminated winged catheter securing tape as recited in claim 9 wherein said nonadhesive strip is aligned beneath said nonadhesive segment.

11. The laminated winged catheter securing tape as recited in claim 9 further comprising an overlay tape having an upper and a lower surface, wherein said lower surface of said overlay tape is adhesive and the ends of said overlay tape extend beyond the ends of said tape base; and,
   wherein said overlay tape is adhesively attached to at least part of said upper surface of said tape base.

\* \* \* \* \*